(12) United States Patent
Li et al.

(10) Patent No.: US 11,312,669 B2
(45) Date of Patent: Apr. 26, 2022

(54) OLIGOMERIZATION OF OLEFINS

(71) Applicant: ExxonMobil Chemical Patents Inc., Baytown, TX (US)

(72) Inventors: Shiwen Li, Etterbeek (BE); Alan A. Galuska, Ellijay, GA (US); Jennifer A. Carvajal Diaz, Spring, TX (US); Mika L. Shiramizu, Houston, TX (US); Wenyih F. Lai, Bridgewater, NJ (US); Lara A. Truter, Eindhoven (NL)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/284,684

(22) PCT Filed: Sep. 26, 2019

(86) PCT No.: PCT/US2019/053092
§ 371 (c)(1),
(2) Date: Apr. 12, 2021

(87) PCT Pub. No.: WO2020/081208
PCT Pub. Date: Apr. 23, 2020

(65) Prior Publication Data
US 2021/0355047 A1 Nov. 18, 2021

Related U.S. Application Data

(60) Provisional application No. 62/746,803, filed on Oct. 17, 2018.

(30) Foreign Application Priority Data

Nov. 13, 2018 (EP) ..................................... 18205825

(51) Int. Cl.
*C07C 2/12* (2006.01)
*B01J 29/70* (2006.01)

(52) U.S. Cl.
CPC .............. *C07C 2/12* (2013.01); *B01J 29/7046* (2013.01); *B01J 29/7096* (2013.01); *B01J 2229/36* (2013.01); *C07C 2529/70* (2013.01)

(58) Field of Classification Search
CPC .............. B01J 2229/123; B01J 2229/18; B01J 2229/20; B01J 2229/42; B01J 29/7076;
(Continued)

(56) References Cited

U.S. PATENT DOCUMENTS

| 4,076,842 A | 2/1978 | Plank et al. |
| 4,870,038 A | 9/1989 | Page et al. |

(Continued)

FOREIGN PATENT DOCUMENTS

| WO | 2006-133967 A | 12/2006 |
| WO | 2020-081208 A | 4/2020 |

(Continued)

OTHER PUBLICATIONS

Claude, M.C., et al., "Dimethyl Branching of Long n-Alkanes in the Range from Decane to Tetracosane on Pt/H-ZSM-22 Bifunctional Catalyst", Journal of Catalysis, vol. 203, pp. 213-231, 2001.

(Continued)

*Primary Examiner* — Sharon Pregler
(74) *Attorney, Agent, or Firm* — ExxonMobil Chemical Patents Inc.—Law Department

(57) ABSTRACT

A process for olefin oligomerization can include: contacting a feedstock comprising at least one $C_3$ to $C_{20}$ olefin/paraffin under oligomerization conditions in the presence of a Si/Al ZSM-23 catalyst having no amine treatment and a $Si/Al_2$ molar ratio of 20 to 60 and/or a Si/Al/Ti ZSM-23 catalyst having no amine treatment, a $Si/Al_2$ molar ratio of 20 to 60, and a Ti/Al molar ratio of 0.1 to 3; and recovering an oligomeric product comprising dimers having a branching index of less than 2.1, trimers having a branching index of (Continued)

less than 2.1, and tetramers having a branching index of less than 2.1.

21 Claims, 3 Drawing Sheets

(58) Field of Classification Search
CPC ..... B01J 29/7092; B01J 29/7096; C07C 2/12; C07C 2/64; C07C 303/06; C07C 11/02; C07C 15/107; C07C 2529/70; C07C 309/31; C07C 45/28; C07C 45/50; C07C 51/16
See application file for complete search history.

(56) References Cited

U.S. PATENT DOCUMENTS

| | | | |
|---|---|---|---|
| 5,026,933 | A | 6/1991 | Blain et al. |
| 5,250,484 | A | 10/1993 | Beck et al. |
| 5,284,989 | A | 2/1994 | Apelian et al. |
| 5,332,566 | A | 7/1994 | Moini |
| 5,672,800 | A | 9/1997 | Mathys et al. |
| 5,849,972 | A | 12/1998 | Vicari et al. |
| 6,008,181 | A | 12/1999 | Cripe et al. |
| 6,020,303 | A | 2/2000 | Cripe et al. |
| 6,060,443 | A | 5/2000 | Cripe et al. |
| 6,143,942 | A | 11/2000 | Wim et al. |
| 6,380,143 | B1 | 4/2002 | Kvietok et al. |
| 7,238,844 | B2 | 7/2007 | Mathys et al. |
| 7,345,212 | B2 * | 3/2008 | Beadle .................. C07B 37/02 585/520 |
| 7,425,662 | B2 | 9/2008 | Stanat et al. |
| 7,759,533 | B2 | 7/2010 | Cheng et al. |
| 8,500,991 | B2 | 8/2013 | Lai et al. |
| 8,883,698 | B2 | 11/2014 | Scheibel et al. |
| 2004/0242948 | A1 | 12/2004 | Georges et al. |
| 2009/0093663 | A1 | 4/2009 | Cheng et al. |
| 2009/0312583 | A1 | 12/2009 | Marcus et al. |
| 2010/0248944 | A1 * | 9/2010 | Cheng ................. B01J 29/7076 502/73 |
| 2017/0355651 | A1 | 12/2017 | Reeker et al. |

FOREIGN PATENT DOCUMENTS

| | | |
|---|---|---|
| WO | 2020-081210 A | 4/2020 |
| WO | 2020-081212 A | 4/2020 |

OTHER PUBLICATIONS

Chauvin Y., et al., "The IFP Dimersol process for dimerization of C3 and C4 olefinic cuts", Chem. Ind. pp. 375-378, 1974.

Nicholas, C. P., "Applications of light olefin oligomerization to the production of fuels and Chemicals", Applied Catalysis A, General vol. 543, pp. 82-97, 2017.

Liu, W., et al., "Effects of Si02/Al203 Ratio on Physicochemical Properties and Catalytic Performance of the Non-templated ZSM-5 Zeolite", Advanced Materials Research. Trans. Tech. Publications, vol. 197-198, pp. 992-995, 2011.

* cited by examiner

OLIGOMERIZATION OF OLEFINS

PRIORITY

This application is a National Phase Application claiming priority to PCT Application Serial No. PCT/US2019/053092 filed Sep. 26, 2019, which claims the benefit of U.S. Provisional Application No. 62/746,803, filed Oct. 17, 2018, and European Application No.18205825.5, filed Nov. 13, 2018, the disclosures of which are incorporated herein by reference.

FIELD

The present disclosure relates to olefin oligomerization.

BACKGROUND OF THE INVENTION

The condensation reaction of an olefin or a mixture of olefins to form higher molecular weight products is widely known and practiced. This type of condensation reaction is referred to herein as an oligomerization reaction or process, and the products are low molecular weight oligomers which are formed by the condensation of up to 12, typically 2, 3 or 4, but up to 5, 6, 7, or even 8 olefin molecules with each other. "Oligomerization" refers to a process for the formation of oligomers and/or polymers. Low molecular weight olefins (such as, for example, ethylene, propene, 2-methylpropene, 1-butene and 2-butenes, pentenes and hexenes) may be converted by oligomerization over, for example, a solid phosphoric acid catalyst (commonly referred to as "sPa" catalyst) or a molecular sieve catalyst (e.g., a zeolite catalyst), to an oligomer product.

The products of olefin oligomerization are usually mixtures of, for example, olefin dimers, trimers, and higher oligomers. Further, each olefin oligomer is itself usually a mixture of isomers, both skeletal and in double bond location. Highly branched isomers are less reactive than linear or lightly branched materials in many of the downstream reactions for which the oligomers are used as feedstocks. This is also true of isomers in which access to the double bond is sterically hindered. In this specification, the olefin types of the oligomers are denominated according to the degree of substitution of the double bond, as follows:

Type I: R—CH═CH2, mono-substituted
Type II: R—CH═CH—R, disubstituted
  Type III: RRC═CH2, disubstituted
  Type IV: RRC═CHR, trisubstituted
  Type V: RRC═CRR, tetrasubstituted wherein R represents an alkyl group, each R being the same or different. Type I compounds are sometimes described as α- or vinyl olefins and Type III as vinylidene olefins. Type IV is sometimes subdivided to provide a Type IVA, in which access to the double bond is less hindered, and Type IVB where it is more hindered.

The degree of branching and double bond Type distribution affect some properties and performance of the olefin derivatives, e.g., the low temperature performance and volatility when converted to alcohols and subsequently to plasticizers.

The degree of branching and mixture of double bond types also affect the reactivity of the oligomer olefins to alkylation and, especially, oxonation. Types I and II have excellent to reactivity, Type III fair reactivity, Type IVA good reactivity, and types IVB and V poor reactivity. In alkylation, reactivity is affected by the ease of protonation of the more readily approached, less hindered, double bonds of the preferred structures. Similar effects apply to the reactivity of the oligomer olefins to oxonation, the low branching and less hindered double bonds allowing the molecules to be converted to aldehydes and alcohols rather than being hydrogenated to paraffins. Oligomer products are valuable components of high-octane gasoline blending stock that may be used or blended into a distillate type liquid fuel or as a lubricant, or as a starting material for the production of chemical intermediates and end-products. Such chemical intermediates and end-products include high purity hydrocarbon fluids or solvents, alcohols, detergents/surfactants, and esters such as plasticizer esters and synthetic lubricants.

Furthermore, detergent products obtainable from the products of alkylation of the olefinic oligomer products, especially those having 10 or more carbon atoms, having low Type IVB and V contents and low degrees of branching, would have numerous advantages in use. These include better hard water solubility, and better biodegradability resulting from the lower levels of quaternary carbons.

A number of catalysts may be used in such oligomerization processes. For example, industrial oligomerization reactions employing molecular sieve catalysts are generally performed in a plurality of tubular or chamber reactors, similar to those processes employing sPa catalysts. With sPa catalysts, the pressure drop over the catalyst bed(s) increases gradually over the duration of the run, due to coking and/or swelling of the catalyst pellets and the reactor run is typically terminated when a maximum allowable pressure drop over the reactor is reached. Molecular sieve catalysts do not show pressure drop increases similar to sPa catalysts. Oligomerization reactors using molecular sieve catalysts are therefore characterized by longer reactor run lengths and are typically decommissioned when the catalyst selectivity and activity has dropped to an unacceptably low level.

U.S. Pat. No. 7,425,662 and International Appl. Pub. No. WO2003/082780 in use, for example, ZSM-22 and ZSM-23 zeolite catalysts that have been treated with a bulky amine to enhance the reaction selectivity. However, the amine is essentially chemisorbed to the acidic sites of the zeolite catalyst. The amines then desorb during the reaction because of high reactor temperatures causing a loss of catalyst selectivity to lower branched olefins. The desorbed amines are also in the reaction product and need to be removed before further processing. Further, regeneration of the catalyst to add the bulky amines and return the reaction selectivity is not straightforward. Accordingly, additional catalysts with easier implementation and regeneration while maintaining a high selectivity towards oligomer product are desired.

SUMMARY OF THE INVENTION

The present disclosure relates to olefin oligomerization. More specifically, the present invention relates to oligomerization processes that utilize a ZSM-23 catalyst having no amine treatment and a Si/Al$_2$ molar ratio of 20 to 60, which demonstrates high selectivity to oligomer products without the drawbacks of the amine treatment.

A first example embodiment of the present invention is a process for olefin oligomerization, the process comprising: contacting a feedstock comprising at least one $C_3$ to $C_{20}$ olefin/paraffin under oligomerization conditions in the presence of a Si/Al ZSM-23 catalyst having no amine treatment and a Si/Al$_2$ molar ratio of 20 to 60 and/or a Si/Al/Ti ZSM-23 catalyst having no amine treatment, a Si/Al$_2$ molar ratio of 20 to 60, and a Ti/Al molar ratio of 0.1 to 3; and recovering an oligomeric product comprising dimers having a branching index (BI) of less than 2.1, or within a range from 0.5, or 1.0, or 1.1, or 1.2, or 1.3 to 1.6, or 1.8, or 2.0, or 2.1; trimers having a branching index of less than 2.1, or within a range from 0.5, or 1.0, or 1.1, or 1.2, or 1.3 to 1.6, or 1.8, or 2.0, or 2.1; and tetramers having a branching index of less than 2.1, or within a range from 0.5, or 1.0, or 1.1, or 1.2, or 1.3 to 1.6, or 1.8, or 2.0, or 2.1. Such dimers, trimers, and tetramers, etc. may also generally be referred to as an "oligomer product".

Detergent formulations can be made from surfactants derived from the oligomer products described herein. Detergent formulations comprise an aqueous fluid; and a reaction product of one or more oligomer products, the reaction product comprising a hydrophobic portion and a polar head group bonded to the hydrophobic portion; wherein an olefin moiety in the one or more oligomer products reacts to produce the hydrophobic portion; and wherein the one or more oligomer products have a Branch Index ranging from 0.5 and 2.1 and branching is retained in the hydrophobic portion of the reaction product; wherein the surfactant is present in the aqueous fluid at a concentration ranging from about 10 wt % to about 80 wt %.

In one embodiment is a detergent formulation comprising: 0 wt % to 30 wt % $C_8$ surfactant, 40 wt % to 85 wt % $C_{10-13}$ surfactant, 0 wt % to 30 wt % $C_{14-16}$ surfactant, and 0 wt % to 10 wt % $C_{17+}$ surfactant, based on the total weight of the detergent, wherein each surfactant has a branching index of less than 2.1, preferably 1.5 or less.

Yet another embodiment is a detergent formulation comprising: 0 wt % to 15 wt % $C_6$ surfactant, 0 wt % to 15 wt % $C_9$ surfactant, and 10 wt % to 70 wt % $C_{12+}$ surfactant, wherein each surfactant has a branching index of less than 2.1, preferably 1.5 or less.

Another embodiment is a detergent formulation comprising: 0 wt % to 30 wt % $C_6$ surfactant, 0 wt % to 30 wt % $C_9$ surfactant, 40 wt % to 85 wt % $C_{12}$ surfactant, wherein each surfactant has a branching index of less than 2.1, preferably 1.5 or less.

Yet another embodiment is a detergent formulation comprising: 10 wt % to 70 wt % $C_{10}$ surfactant, 0 wt % to 15 wt % $C_{15}$ surfactant, and 0 wt % to 15 wt % $C_{20+}$ surfactant, wherein each surfactant has a branching index of less than 1.8, preferably 1.5 or less.

Another embodiment is a detergent formulation comprising: 40 wt % to 85 wt % $C_{10}$ surfactant, 0 wt % to 30 wt % $C_{15}$ surfactant, 0 wt % to 30 wt % $C_{20}$ surfactant, and 0 wt % to 10 wt % $C_{25+}$ surfactant, wherein each surfactant has a branching index of less than 1.8, preferably 1.5 or less.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure relates to olefin oligomerization. More specifically, the present invention relates to oligomerization processes that utilize a ZSM-23 catalyst having no amine treatment and a $Si/Al_2$ molar ratio of 20 to 60, which demonstrates high selectivity to oligomer products without the drawbacks of the amine treatment.

Figure 1:
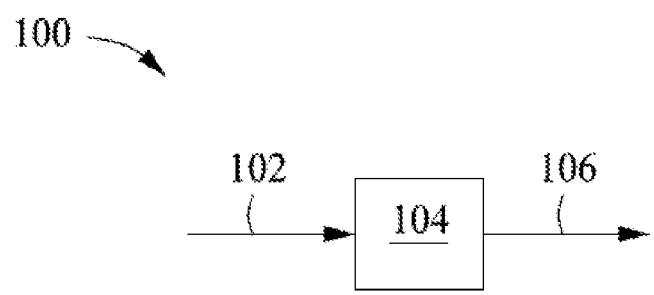
FIG. 1 illustrates a first example oligomerization process of the present invention.

FIG. 1 illustrates a first example oligomerization process 100 of the present invention. A feedstock 102 is fed into a reactor(s) 104 that contains oligomerization catalyst. The reactor(s) 104 is maintained at oligomerization conditions (described further herein) to facilitate catalyzed oligomerization of the feedstock 102 to produce an oligomer product 106. In one example, the feedstock 102 comprises primarily $C_n$ and $C_{2n}$ olefins/paraffins and the oligomer product 106 comprises $C_{3n}$ oligomers. Other example feedstocks and oligomer products are described herein.

Figure 2:
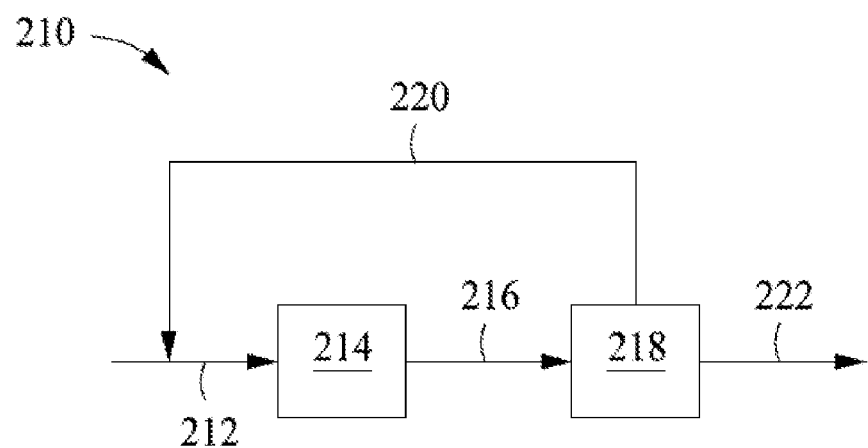
FIG. 2 illustrates a second example oligomerization process of the present invention.

FIG. 2 illustrates a second example oligomerization process 210 of the present invention. A feedstock 212 is fed into a reactor(s) 214 that contains oligomerization catalyst. The reactor(s) 214 is maintained at oligomerization conditions (described further herein) to facilitate catalyzed oligomerization of the feedstock 212 to produce an oligomer product 216. The oligomer product is then separated (e.g., in a distiller or recovery tower 218) to produce a recycle stream 220 and a product stream 222. The recycle stream 220 is fed back into the reactor(s) 214. As illustrated, it is entrained with the feedstock 212. In one example, the feedstock 102 comprises primarily $C_n$ and $C_{2n}$ olefins/paraffins, the oligomer product 106 comprises a mixture of $C_n$, $C_{2n}$, and $C_{3n}$, the recycle stream comprises $C_n$ and $C_{2n}$, and the product stream comprises $C_{3n}$. Other example feedstocks and oligomer products are described herein.

Alternatively, to FIG. 2, the recycle stream could be fed to a second reactor containing oligomerization catalyst and maintained at oligomerization conditions (described further herein).

Figure 3:
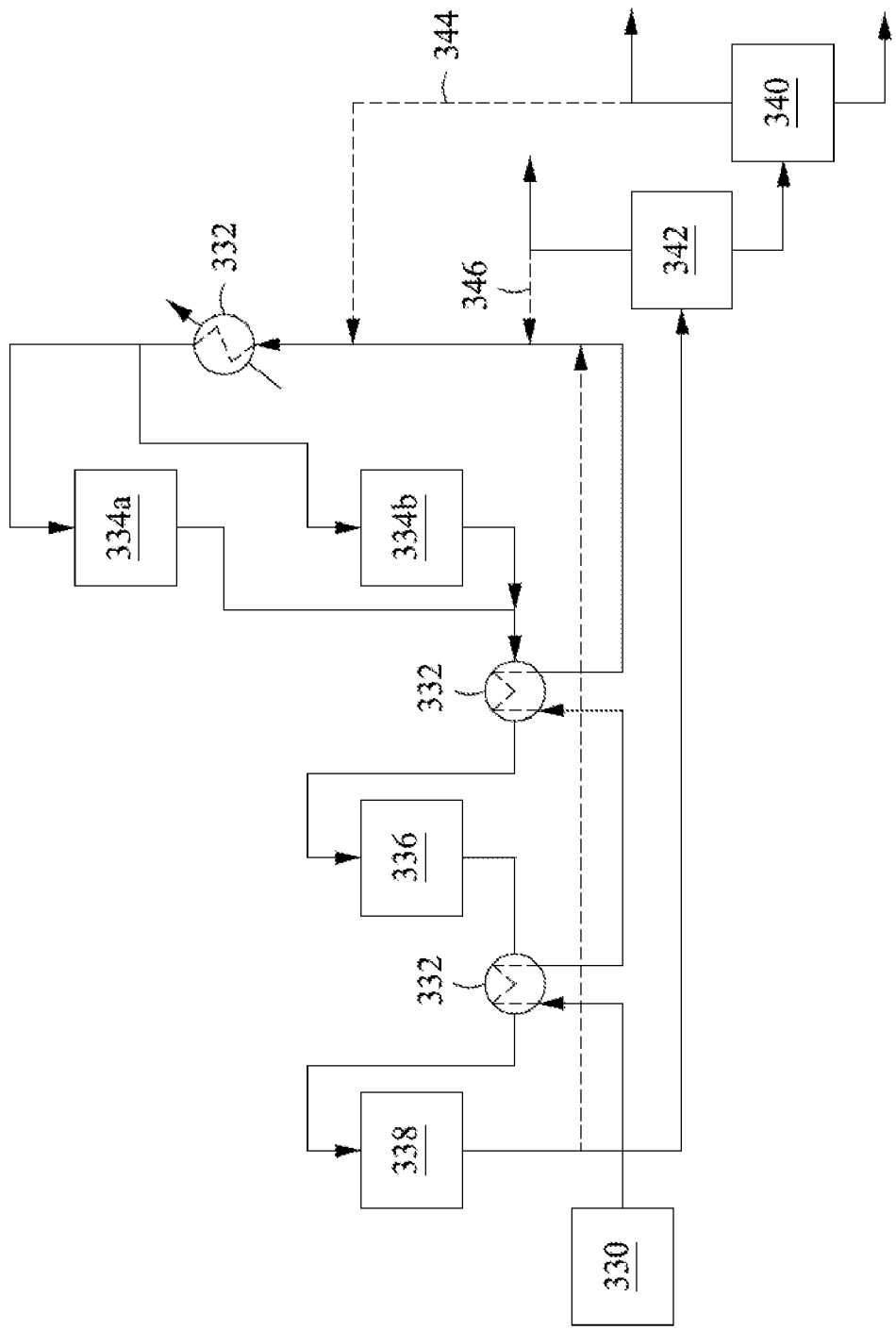
FIG. 3 is a flow diagram of a process of oligomerization, predominantly directed to production and recovery of a dimer product.
Figure 4:
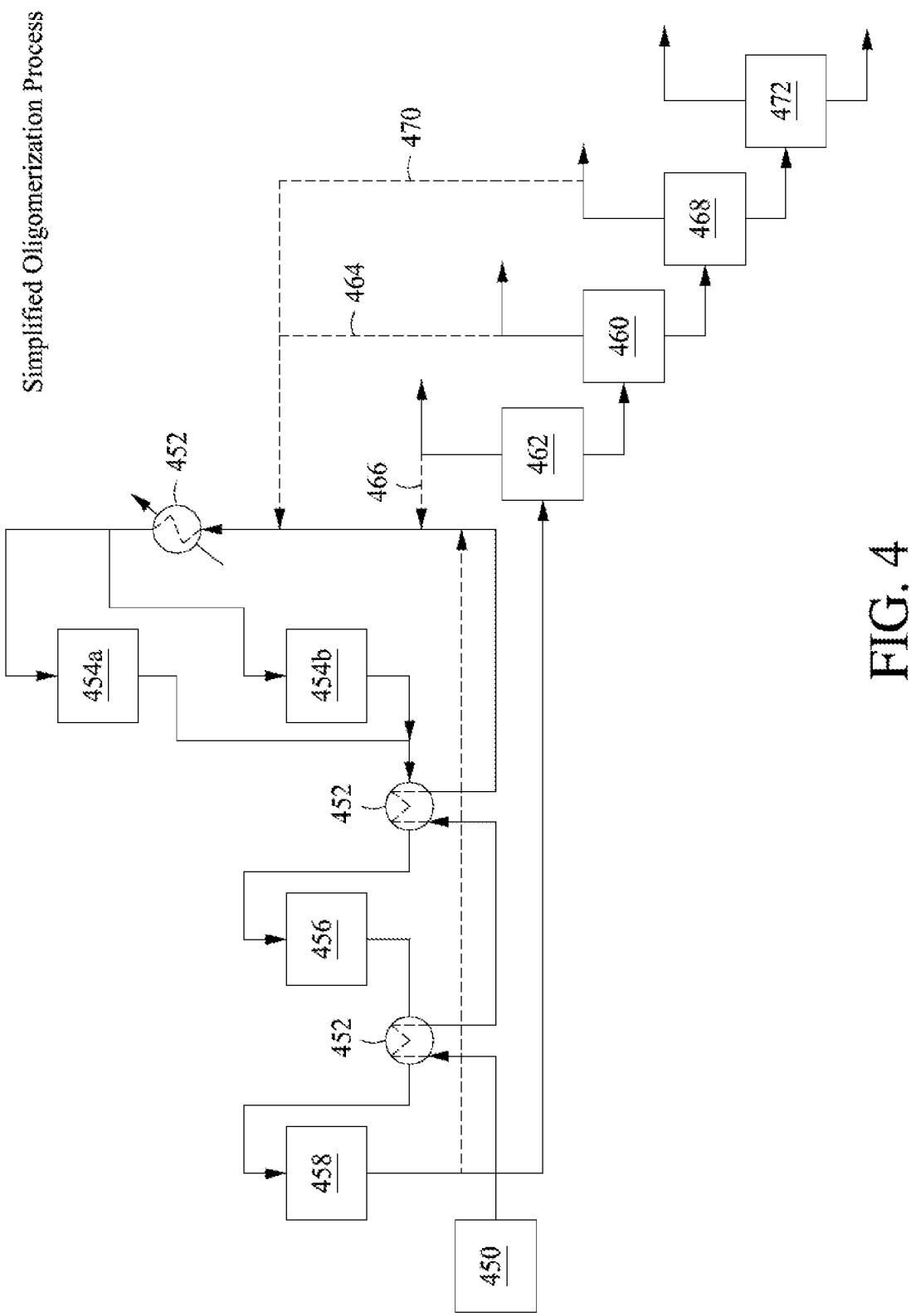
FIG. 4 is a flow diagram of a process of oligomerization, predominantly directed to production and recovery of a trimer product.

Two specific examples of reactor and separation embodiments are provided in FIGS. 3 and 4. These examples may be adapted by those skilled in the art to accommodate other reaction and separation needs.

Referring to FIG. 3, a $C_4$, $C_5$, or mixed olefins/paraffins feedstock containing at least one of $C_4$ and $C_5$ olefins 330 is fed in via heat-exchangers 332 to reactors 334a, 334b, in parallel and subsequently to reactors 336, 338 in series. The product from reactor 338 is fed to the product recovery tower 340 via de-butanizer tower 342. $C_8$ dimer (from butene) is taken off as overhead, with optional recycle via line 344 to reactors 334a and 334b if the $C_{12+}$ product is to be maximized The de-butanizer tower overheads may optionally be recycled to the reactors 334a and 334b via line 346.

Referring now to FIG. 4, a $C_4$, $C_5$, or mixed olefins/paraffins feedstock containing at least one of $C_4$ and $C_5$ olefins 450 is fed in via heat-exchangers 452 to reactors 454a, 454b, in parallel and subsequently to reactors 456, 458 in series. The product from reactor 458 is fed to the $C_8$ product recovery tower 460 via de-butanizer tower 462. $C_8$ dimer (from butene) is taken off from tower 460 as overhead, with optional recycle via line 464 to reactors 454a and 454b if the $C_{12+}$ product is to be maximized The de-butanizer tower overheads may optionally be recycled to the reactors 454a and 454b via line 466.

The bottoms product from tower 460 is fed to the $C_{12}$ product recovery tower 468, $C_{12}$ product being taken off as overhead, with optional recycle via line 470 if the $C_{16+}$ product is to be maximized The bottoms product from tower 468 is fed to product recovery tower 472, where $C_{12}$ to $C_{14}$ product is taken off as overheads with $C_{16}$ to $C_{20}$ product being taken off as bottoms product.

Feedstock/Feedstream

The at least one feedstock or feedstream comprises olefins, paraffins, and other components. As used herein and unless otherwise specified, "feedstock(s)" and "feedstream(s)" may be used interchangeably. The at least one feedstream may comprise olefins having from 2 to 15 carbon atoms, such as, for example, from 3 to 6 carbon atoms and one or more paraffins. As used herein, "olefins" refers to any of the unsaturated hydrocarbons (e.g., compounds consisting essential of hydrogen and carbon atoms) having the formula $C_nH_{2n}$, wherein n is an integer from 1 to 25, typically, from 1 to 15, preferably, from 3 to 6. As used herein, "paraffins" refers to any of the saturated hydrocarbons having the formula $C_nH_{2n+2}$, wherein n is an integer from 1 to 25, typically, from 1 to 15, preferably, from 3 to 6. Additionally, the feedstream may comprise an oligomer, such as, for example, a dimer, for example, one provided by recycling a part of a product stream. As used herein, the terms "olefin/paraffin" and "olefins/paraffins" refers to a composition comprising at least one olefin and, optionally, at least one paraffin.

The feedstream may comprise olefins/paraffins having the same or different number of carbon atoms.

The feedstream may comprise one or more of propene, butenes, pentenes, hexenes, their isomers, paraffins having the same or different carbon numbers, and mixtures thereof. The process is especially useful for the oligomerization of feedstreams comprising propene, butenes, pentenes, their isomers, other components, and mixtures thereof.

As used herein, "oligomer(s)" or "oligomer product" refers to a polymer molecule (or a mixture of polymer molecules) made from a few monomer units such as, for example, a dimer, a trimer, a tetramer, and mixtures thereof. "Oligomer(s)" refers to a polymer molecule (or a mixture of polymer molecules) having 20 carbon atoms or less, alternatively, 15 carbon atoms or less, alternatively, 10 carbon atoms or less, alternatively, 9 carbon atoms or less, and alternatively, 8 carbon atoms or less. As used herein, "oligomerization process" refers to any process of catalytically joining monomer units to form the oligomer(s) as defined above. The oligomerization process is used synonymously herein with "polymerization process." As used herein, the term "oligomerization conditions" refers to any and all those variations of equipment, conditions (e.g., temperatures, pressures, and flow rates), materials, and reactor schemes that are suitable to conduct the oligomerization process to produce the oligomer(s) as known, and applied in the art and discussed more below.

The olefins to be oligomerized may be one or more of $C_3$-$C_{15}$ olefins or mixtures thereof including one or more paraffins having the same or different carbon number, alternatively, $C_3$-$C_6$ olefins or mixtures thereof, including one or more paraffins having the same or different carbon number, and preferably, $C_3$-$C_5$ olefins or mixtures thereof including one or more paraffins having the same or different carbon number.

The feedstream may comprise 45 wt % or more olefins, alternatively, 50 wt % or more olefins, alternatively, 60 wt % or more olefins, alternatively, 70 wt % or more olefins, and preferably, 80 wt % or more olefins, based upon the total weight of the feedstreams(s).

Alternatively, the at least one feedstream may comprise 45 wt % or more olefins/paraffins, alternatively 60 wt % or more olefins/paraffins, alternatively 75 wt % or more olefins/paraffins, alternatively, 80 wt % or more olefins/paraffins, alternatively, 85 wt % or more olefins/paraffins, alternatively, 90 wt % or more olefins/paraffins, and alternatively, 95 wt % or more olefins/paraffins, based upon the total weight of the feedstream(s).

The olefins/paraffins may have the same or different carbon number or may be a mixture of olefins/paraffins that have the same and different carbon numbers. For example, the at least one feedstream comprises the ranges stated above of propylene and propane but may also have other smaller amounts of other olefins/paraffins having different carbon numbers, such as, for example, butanes and butenes, ethanes and ethylenes, and the like.

Alternatively, the at least one feedstream may comprise 60 wt % or more combined $C_3$ olefins/paraffins, alternatively, 70 wt % or more combined $C_3$ olefins/paraffins, alternatively, 80 wt % or more combined $C_3$ olefins/paraffins, alternatively, 85 wt % or more combined $C_3$ olefins/paraffins, alternatively, 90 wt % or more combined $C_3$ olefins/paraffins, and alternatively, 95 wt % or more combined $C_3$ olefins/paraffins, based upon the total weight of the feedstream(s).

Alternatively, the at least one feedstream may comprise 60 wt % or more combined $C_4$ olefins/paraffins, alternatively, 70 wt % or more combined $C_3$ olefins/paraffins, alternatively, 80 wt % or more combined $C_4$ olefins/paraffins, alternatively, 85 wt % or more combined $C_4$ olefins/paraffins, alternatively, 90 wt % or more combined $C_4$ olefins/paraffins, and alternatively, 95 wt % or more combined $C_4$ olefins/paraffins, based upon the total weight of the feedstream(s).

Alternatively, the at least one feedstream may comprise 60 wt % or more combined $C_5$ olefins/paraffins, alternatively, 70 wt % or more combined $C_5$ olefins/paraffins, alternatively, 80 wt % or more combined $C_3$ olefins/paraffins, alternatively, 85 wt % or more combined $C_5$ olefins/paraffins, alternatively, 90 wt % or more combined $C_5$ olefins/paraffins, and alternatively, 95 wt % or more combined $C_5$ olefins/paraffins, based upon the total weight of the feedstream(s).

The feedstream may be free of aromatic hydrocarbon compounds that consist solely of hydrogen and carbon or be substantially free of aromatic hydrocarbon compounds that consist solely of hydrogen and carbon. As used herein, "substantially free" refers to 25 wt % or less of the aromatic hydrocarbon compound present in the feedstream(s), alternatively, 15 wt % or less, alternatively, 10 wt % or less, alternatively, 5 wt % or less, and preferably, 1 wt % or less, based upon the total weight of the feedstream(s).

Additionally, the feedstream may comprise isomers of any of the constituents found therein. As used herein, "isomer" refers to compounds having the same molecular formula but different structural formula. Examples may be structural isomers, stereoisomers, enantiomers, geometrical isomers, and the like. Typically, the feedstream may comprise at least one isomer of the olefins/paraffins) or other constituents in the feedstream.

The feedstream may also comprise contaminants or compounds that may hinder catalyst life or productivity. These may include nitrogen, sulfur, chlorine, oxygen containing compounds, and mixtures thereof. Examples of nitrogen containing compounds include nitriles (e.g., acetonitrile, propionitrile, and the like), ammonia, amides, amines, pyridines, imides, cyanates, pyrroles, pyrrolidones, and mixtures thereof.

The feedstream may also comprise other compounds that may hinder catalyst life or productivity. These may include linear and cyclic dienes such as butadiene, pentadiene, cyclo pentadiene, and mixtures thereof.

Examples of suitable feedstreams include untreated refinery streams such as Fluidized Catalytic Cracking (FCC), coker, and pygas streams as well as aromatics-containing streams, such as, for example, reformates.

Other examples include Raffinate-1 (RAF-1), Raffinate-2 (RAF-2), and/or Raffinate-3. Typically, Raffinate-1, Raffinate-2, and Raffinate-3 may be regarded as stages in the processing of crude, generally, $C_4$ streams. Examples of Raffinate products that can be used as feedstreams can be found in U.S. Pat. No. 7,759,533, which is incorporated herein by reference. These streams are usually from olefin steam crackers but may also come from refinery cat-crackers, Butane Dehydrogenation Units, or Gas to Olefin (GTO) Units, or Fisher-Tropsch Units in which case they generally contain the same components but in different proportions with some variation understood by a skilled artisan. The first stage of the process is to remove, by generally solvent extraction or hydrogenation (for example, in a Selective Butadiene Hydrogenation unit) the butadiene, which may be as much as 40 wt % to 45 wt % of the stream. After the butadiene content is substantially reduced in the $C_4$ stream to, for example, 10000 wt ppm or less diene content, alternatively, 5000 wt ppm or less diene content, alternatively, 1000 to wt ppm or less diene content, alternatively, 200 wt ppm or less diene content, and alternatively, 10 wt ppm or less diene content, based upon the total weight of the feedstream(s), the remaining product is Raffinate-1. It generally consists of isobutylene, the two normal isomers, butene-1 and butene-2, and smaller quantities of butanes and other compounds. Removal of the isobutylene, usually by reaction with methanol to produce MTBE, the reaction with ethanol to produce ETBE, the production of di-isobutylene (DIB), reaction with water to produce tertiary butyl alcohol (TBA) and the formation of alkyl esters by contact with sulphuric acid produces Raffinate-2. Raffinate 3 (RAF-3) is less common but may also be used. Raffinate 3 may be obtained after separation of 1-butene from Raffinate 2 with a residual 1-butene content of 1%.

Examples of suitable $C_3$ olefin/paraffin containing feedstreams include untreated $C_3$ rich refinery streams such as "dilute" or "refinery grade" propylene from a Fluidized Catalytic Cracker (FCC), $C_3$ rich stream from a steam cracker, $C_3$ rich streams from the production of "chemical grade" or "polymer grade" propylene, $C_3$ rich streams from refinery gas recovery units, $C_3$ rich streams from Propane Dehydrogenation Units, $C_3$ rich streams from Gas to Olefin (GTO) Units, or Fisher-Tropsch Units, and $C_3$ rich return streams from polypropylene producing units.

The feedstream may comprise a mixed $C_3/C_4$ FCC light olefin/paraffin stream that typically comprises ethane, ethylene, propane, propylene, isobutane, n-butane, butenes, pentanes, and other optional components. A specific example of such a feedstream is provided in Table 1.

TABLE 1

| Component | Wt % | Mol % |
|---|---|---|
| ethane | 3.3 | 5.1 |
| ethylene | 0.7 | 1.2 |
| propane | 4.5 | 15.3 |

TABLE 1-continued

| Component | Wt % | Mol % |
|---|---|---|
| propylene | 42.5 | 46.8 |
| isobutane | 12.9 | 10.3 |
| n-butane | 3.3 | 2.6 |
| butenes | 22.1 | 18.3 |
| pentanes | 0.7 | 0.4 |

The feedstream may comprise a $C_3$ rich FCC stream that typically comprises ethane, ethylene, propane, propylene, isobutane, isobutene, and other optional components. A specific example of such a feedstream is provided in Table 2.

TABLE 2

| Component | Wt % | Mol % |
|---|---|---|
| ethane | 2.8 | 3.9 |
| ethylene | 0.7 | 1.0 |
| propane | 17.4 | 16.6 |
| propylene | 76.7 | 76.7 |
| isobutane | 1.7 | 1.2 |
| isobutene | 0.5 | 0.4 |
| butenes | 0.2 | 0.2 |

The feedstream comprises a $C_3$ rich olefin/paraffin containing stream that is a mixture of refinery $C_3$ rich streams and diluent stream(s) that typically comprises ethane, ethylene, propane, propylene, isobutane, isobutene, and other optional components. A specific to example of such a feedstream is provided in Table 3.

TABLE 3

| Component | Wt % | Mol % |
|---|---|---|
| ethane | 3 | 4.6 |
| ethylene | 0.1 | 0.2 |
| propane | 20.3 | 21.3 |
| propylene | 439 | 48.1 |
| isobutane | 20.2 | 16.1 |
| isobutene | 0.2 | 0.2 |
| butenes | 2.4 | 2.0 |
| butane | 6.5 | 5.3 |
| pentanes | 3.5 | 2.3 |

The feedstream comprises a $C_4$ rich olefin/paraffin containing stream. A specific example of such a feedstream is provided in Table 4.

TABLE 4

| Component | Wt % |
|---|---|
| n-butene | 30-50 |
| butane | 40-60 |
| isobutane | 5-20 |

The feedstream comprises a $C_4$ rich olefin/paraffin containing stream. A specific example of such a feedstream is provided in Table 5.

TABLE 5

| Component | Wt % |
|---|---|
| n-butene | 15-35 |
| butane | 30-50 |

TABLE 5-continued

| Component | Wt % |
|---|---|
| isobutane | 5-20 |
| octene | 15-35 |

Examples of Raffinate feedstream are provided in Table 6.

TABLE 6

| Component | Raffinate 1 after solvent extraction (wt %) | Raffinate 1 after hydrogenation (wt %) | Raffinate 2 after solvent extraction (wt %) | Raffinate 2 after hydrogenation (wt %) |
|---|---|---|---|---|
| butadiene | 0-2 | 0-2 | 0-1 | 0-1 |
| $C_4$ | 0-0.5 | 0-0.5 | 0-0.5 | 0-0.5 |
| 1-butene | 20-50 | 50-95 | 25-75 | 75-95 |
| 2-butene | 10-30 | 0-20 | 15-40 | 0-20 |
| isobutene | 0-55 | 0-35 | 0-5 | 0-5 |
| n-butane | 0-55 | 0-10 | 0-55 | 0-10 |
| isobutane | 0-1 | 0-1 | 0-2 | 0-2 |

Optionally, the feedstream(s) may comprise a diluent. The diluent may comprise any suitable hydrocarbon such as alkanes or a mixture comprising at least one alkane. The to alkanes may be represented the general formula: CnH2n+2, wherein n is a number from 1 to 20, alternatively, from 1 to 10, alternatively, from 1 to 5, and alternatively, from 3 to 4. Examples may include methane, ethane, propane, butane, pentane, and mixtures thereof. When the diluent is present, the feedstream(s) may comprise at least 10%, at least 25%, at least 30%, at least 35%, or at least 40% of the diluent, for example, the alkane such as propane and/or butane, based upon the total volume of the feedstream. Alternatively stated, the diluent may be present in the feedstream in the range from 10% to 40%, alternatively, from 10% to 35%, and alternatively, from 20% to 35% based upon the total volume of the feedstream.

The diluent may also be delivered to the reactor(s) through separate feedstreams. When fed separately, the diluent may be fed in amounts to be equivalent to the embodiments wherein the diluent is co-fed with the feedstream. These amounts may not necessarily be the same as the ranges stated above given that more or less of the diluent may be necessary when fed separately to provide an equivalent. In some embodiments, the diluent, when present, may improve reactor continuity.

Reactors, Reaction Conditions, and Oligomerization Catalyst

The reaction system may include one or more of a fixed bed reactor, a packed bed reactor, a tubular reactor, a fluidized bed reactor, a slurry reactor, a continuous catalyst regeneration reactor, and any combination thereof. The reactor(s) may be operated in any combination such as, for example, in series and/or parallel sequence. The reactor(s) may be operated in semi-continuous (i.e., continuous but down for routine maintenance), continuous, and/or batch mode.

The oligomerization conditions may include operating temperatures from 150° C. to 270° C. More typically, the reaction temperature is from 160° C. to 240° C., and alternatively, from 170° C. to 210° C. Close to and above the upper end of the range, deoligomerization rates increase and may predominate over the oligomerization reaction providing an upper limit to practical operation. To mitigate this, the weight hourly space velocity (WHSV) may be increased.

As used herein, "Weight Hour Space Velocity" (WHSV) is a measure of the weight of feedstream flowing per unit weight of the catalyst per hour, weight of the catalyst may be that of molecular sieve or that of formulated molecular sieve extrudates.

The olefin/paraffin WHSV may be in the range of from 5 $hr^{-1}$ to 30 $hr^{-1}$, alternatively 5 $hr^{-1}$ to 10 $hr^{-1}$, alternatively 10 $hr^{-1}$ to 15 $hr^{-1}$, alternatively 15 $hr^{-1}$ to 20 $hr^{-1}$, and alternatively 20 $hr^{-1}$ to 30 $hr^{-1}$.

The pressure may be in the range of from 400 psig to 4000 psig (2860 kPa to 27,680 kPa), and alternatively, from 500 psig to 1500 psig (3550 kPa to 10440 kPa).

In one example, the process is conducted at a temperature of 170° C. to 190° C.; an olefin/paraffin WHSV of 5 $hr^{-1}$ or greater (e.g., 5 $hr^{-1}$ to 10 $hr^{-1}$); and a pressure of 2860-27,680 kPa.

In another example, the process is conducted at a temperature of 190° C. to 210° C.;
an olefin/paraffin WHSV of 10 $hr^{-1}$ or greater (e.g., 10 $hr^{-1}$ to 15 $hr^{-1}$); and a pressure of 2860-27,680 kPa.

In yet another example, the process is conducted at a temperature of 210° C. or greater (e.g., 210° C. to 270° C.); an olefin/paraffin WHSV of 15 $hr^{-1}$ or greater (e.g., 15 $hr^{-1}$ to 30 $hr^{-1}$); and a pressure of 2860-27,680 kPa.

The catalyst can be a Si/Al ZSM-23 catalyst having no amine treatment and a $Si/Al_2$ molar ratio of 20 to 60, alternatively 25 to 55, alternatively 30 to 50, and preferably 30 to 45. Si/Al ZSM-23 catalysts can be prepared using the recipe described in U.S. Pat. Nos. 4,076,842 and 5,332,566. Alternatively, the catalyst can be a Si/Al/Ti ZSM-23 catalyst having no amine treatment and a $Si/Al_2$ molar ratio of 20 to 60, alternatively 25 to 55, alternatively 30 to 50 and a Ti/Al molar ratio of 0.1 to 3, alternatively 0.2 to 2, alternatively 0.3 to 1. Si/Al/Ti ZSM-23 catalysts can be prepared using the recipe described in U.S. Pat. Nos. 4,076,842 and 5,332,566. A combination of the two catalysts can be used. As used herein, the term "ZSM-23 catalyst" is used generally to refer to Si/Al ZSM-23 catalyst, Si/Al/Ti ZSM-23 catalyst, or a combination of Si/Al ZSM-23 catalyst and Si/Al/Ti ZSM-23 catalysts.

The ZSM-23 catalysts can be prepared from extrudates (1 wt % to 90 wt % binder and 10 wt % to 100 wt % zeolite) or from ZSM-23 crystal seeds. Examples of binders include silica, alumina, zirconia, titania, and the like, and mixtures thereof. ZSM-23 catalysts that are crystals can have an aspect ratio of 1 to 5, alternatively 2-4, with a width of less than 0.1 microns and a length of less than 0.3 microns. After the extrudate or the crystal structures are formed, the ZSM-23 catalysts can be calcined in air at 425° C. to 650° C. for 1 hour to overnight.

Optionally, the ZSM-23 catalysts after calcining can be treated. Suitable treatments include, but are not limited to, steaming, acid washing, depositing coke, and any combination thereof.

Steaming can be performed by exposing the ZSM-23 catalysts to steam at 200° C. to 550° C., alternatively 225° C. to 400° C., for 1 hour to 24 hours, alternatively 5 hours to 6 hours, alternatively 1 hour to 4 hours.

Acid washing can be performed by exposing the ZSM-23 catalysts to an aqueous acid solution at 20° C. to 100° C., alternatively 25° C. to 50° C., for 1 hour to 24 hours, alternatively 5 hours to 6 hours, alternatively 1 hour to 4 hours. Suitable acids include, but are not limited to, oxalic acid, malonic acid, succinic acid, glutaric acid, adipic acid, maleic acid, phthalic acid, isophthalic acid, terephthalic acid, fumaric acid, tartaric acid, and the like, and mixtures thereof. The acid may be at any suitable concentration, for example, 1 molar to 4 molar, alternatively 1 molar to 2 molar, alternatively 2 molar to 4 molar.

Depositing coke on the ZSM-23 catalysts can be achieved by exposing the ZSM-23 catalysts to a carbon feedstock under coking conditions. For example, the ZSM-23 catalysts can be exposed to hydrocarbons at 200° C. to 400° C. at 50 bar to 100 bar to deposit coke on the surface of the ZSM-23 catalysts. Examples of hydrocarbons include the feedstocks described herein.

Oligomer Product

The oligomer product may comprise dimers, trimers, tetramers, pentamers, and higher oligomers of the feedstock components. The feedstock components that compose the oligomers may be the same or different. For example, a dimer of $C_3$ and $C_4$ components results in a $C_7$ oligomer. In another example, a dimer of $C_3$ components results in a $C_6$ oligomer.

The oligomer product may comprise one or more $C_6$ to $C_{60}$ oligomers, alternatively one or more $C_6$ to $C_{20}$ oligomers, alternatively one or more $C_6$ to $C_{12}$ oligomers, and alternatively one or more $C_8$ to $C_{16}$ oligomers.

Preferably, the catalyst and oligomerization conditions favor the formation of linear and oligomer product. The degree of branching of the oligomer product as a whole or for individual components is referred to as the "branching index" or "BI." The branching index is an indication of the average number of branches per monomer unit.

Product carbon number distribution and branching index can be measured using an HP-5890 GC equipped by a 30 meter DB-1 column (0.1 mm id) and 0.2 µm film thickness with an $H_2$-GC. The product branching index is calculated following similar method used in U.S. Pat. No. 7,759,533. That is, for $C_8$, $C_{12}$, and/or $C_{16}$ olefins: Branching index equals (0×% linear+1×% monobranched+2×% di-branched+3×% tri-branched)/100; where % linear+% monobranched+% di-branched+% tri-branched=100%.

The oligomer product as a whole may have a branching index of less than 1.8, preferably 1.5 or less (e.g., 1.0 to 1.5). An individual component of the oligomer product (e.g., the $C_{12}$ component or the $C_{16}$ component) may have a branching index of less than 2.1 (e.g., 1.0 to 2.1), preferably 1.8 or less (e.g., 1.0 to 1.8), and more preferably 1.5 or less (e.g., 1.0 to 1.5). For example, the $C_8$ component of an oligomer product that is composed of 10% linear $C_8$, 30% mono-branched $C_8$, 50% di-branched $C_8$, and 10% tri-branched $C_8$ has a branching index of 1.6=[(0*10%)+(1*30%)+(2*50%)+(3*10%)]/100%.

The conversion percentage of feedstock to oligomer may be 20% or greater, alternatively 40% or greater, alternatively 60% or greater, or alternatively 80% or greater.

Within the oligomer product, the concentration of dimers may be 25 wt % to 75 wt %, alternatively 25 wt % to 50 wt %, alternatively 40 wt % to 65 wt %, or alternatively 50 wt % to 75 wt %. Within the oligomer product, the concentration of trimer may be 25 wt % to 50 wt %, alternatively 30 wt % to 45 wt %, or alternatively 25 wt % to 35 wt %. Within the oligomer product, the concentration of tetramer may be 0 wt % to 25 wt %, alternatively 5 wt % to 15 wt %, or alternatively 0 wt % to 10 wt %. Within the oligomer product, the concentration of pentamer and higher oligomers cumulatively may be 0 wt % to 10 wt %, alternatively 0 wt % to 5 wt %, or alternatively 0 wt % to 2 wt %.

In a first example, an oligomer product derived from a $C_4$ feedstock (e.g., Table 4) may comprise 25 wt % to 75 wt % $C_8$ oligomer, 25 wt % to 50 wt % $C_{12}$ oligomer, and 0 wt % to 25 wt % $C_{16}$ oligomer. In a second example, an oligomer product derived from a $C_4$ feedstock (e.g., Table 4) may comprise 35 wt % to 75 wt % $C_8$ oligomer, 25 wt % to 45 wt % $C_{12}$ oligomer, and 5 wt % to 15 wt % $C_{16}$ oligomer. In a third example, an oligomer product derived from a $C_4$ feedstock (e.g., Table 4) may comprise 50 wt % to 75 wt % $C_8$ oligomer, 25 wt % to 35 wt % $C_{12}$ oligomer, and 0 wt % to 10 wt % $C_{16}$ oligomer. Any of the foregoing examples can have a branching index of less than 2.1, preferably 1.8 or less, and more preferably 1.5 or less.

In another example, an oligomer product derived from a $C_3$ feedstock may comprise 25 wt % to 75 wt % $C_6$ oligomer, 25 wt % to 50 wt % $C_9$ oligomer, and 0 wt % to 25 wt % $C_{12}$ oligomer. In a second example, an oligomer product derived from a $C_3$ feedstock may comprise 35 wt % to 75 wt % $C_6$ oligomer, 25 wt % to 45 wt % $C_9$ oligomer, and 5 wt % to 15 wt % $C_{12}$ oligomer. In a third example, an oligomer product derived from a $C_3$ feedstock may comprise 50 wt % to 75 wt % $C_6$ oligomer, 25 wt % to 35 wt % $C_9$ oligomer, and 0 wt % to 10 wt % $C_{12}$ oligomer. Any of the foregoing examples can have a branching index of less than 2.1, preferably 1.8 or less, and more preferably 1.5 or less.

In another example, an oligomer product derived from a $C_5$ feedstock may comprise 25 wt % to 75 wt % $C_{10}$ oligomer, 25 wt % to 50 wt % $C_{15}$ oligomer, and 0 wt % to 25 wt % $C_{20}$ oligomer. In a second example, an oligomer product derived from a $C_5$ feedstock may comprise 35 wt % to 75 wt % $C_{10}$ oligomer, 25 wt % to 45 wt % $C_{15}$ oligomer, and 5 wt % to 15 wt % $C_{20}$ oligomer. In a third example, an oligomer product derived from a $C_5$ feedstock may comprise 50 wt % to 75 wt % $C_{10}$ oligomer, 25 wt % to 35 wt % $C_{15}$ oligomer, and 0 wt % to 10 wt % $C_{20}$ oligomer. Any of the foregoing examples can have a branching index of less than 2.1, preferably 1.8 or less, and more preferably 1.5 or less.

Recycling

Optionally, the oligomer product can be used as feedstock and passed over the catalyst again. The catalyst can be in a different reactor. Alternatively, the same catalyst can be used where the oligomer product is passed back through the reactor optionally diluted with original feedstock.

Because the catalyst described herein often preferentially forms dimers, when a trimer or tetramer is desired, recycling the feedstock allows for monomers to react with dimer and dimers to react with dimers to produce higher concentrations of trimers and tetramers. Because the catalyst described herein also produces light branching the oligomer product after a second pass will have light branching also.

For example, a first oligomer product derived from a $C_4$ feedstock (e.g., Table 4) may comprise 50 wt % to 85 wt % $C_8$ oligomer, 25 wt % to 35 wt % $C_{12}$ oligomer, and 0 wt % to 10 wt % $C_{16}$ oligomer, based on the weight of the feedstock. Then, upon a second pass over the catalyst at suitable oligomerization conditions, the second oligomer product may comprise 0 wt % to 30 wt % $C_8$ oligomer, 45 wt % to 85 wt % $C_{12}$ oligomer, 5 wt % to 55 wt % $C_{16}$ oligomer, and 0 wt % to 10 wt % $C_{20+}$ oligomer. Optionally, before the second pass of the oligomer product over the ZSM-23 catalysts, the first oligomer product can be distilled where only a portion of the first oligomer product is in the second pass. For example, the first oligomer product derived from a $C_4$ feedstock (e.g., Table 4) may comprise 50 wt % to 85 wt % $C_8$ oligomer, 25 wt % to 35 wt % $C_{12}$ oligomer, and 0 wt % to 10 wt % $C_{16}$ oligomer. Then, the first oligomer product can be distilled and the unreacted $C_4$ feedstock and the produced $C_8$ oligomer can be removed from the first oligomer product by distillation. The resultant $C_4/C_8$ mixture can then be all or a portion of the feedstock in the second pass that produced the second oligomer product.

In another example, an oligomer product derived from a $C_4/C_8$ feedstock (e.g., Table 5 or a recycled oligomer product distilled or as is) may comprise 0 wt % to 30 wt % $C_8$ oligomer, 45 wt % to 85 wt % $C_{12}$ oligomer, 5 wt % to 55 wt % $C_{16}$ oligomer, and 0 wt % to 10 wt % $C_{20+}$ oligomer. In yet another example, an oligomer product derived from a $C_4/C_8$ feedstock (e.g., Table 5 or a recycled oligomer product distilled or as is) may comprise 5 wt % to 25 wt % $C_8$ oligomer, 50 wt % to 85 wt % $C_{12}$ oligomer, 10 wt % to 30 wt % $C_{16}$ oligomer, and 0 wt % to 10 wt % $C_{20+}$ oligomer. In another example, an oligomer product derived from a $C_4/C_8$ feedstock (e.g., Table 5 or a recycled oligomer product distilled or as is) may comprise 5 wt % to 25 wt % $C_8$ oligomer, 60 wt % to 85 wt % $C_{12}$ oligomer, 8 wt % to 20 wt % $C_{16}$ oligomer, and 0 wt % to 5 wt % $C_{20+}$ oligomer. Any of the foregoing examples can have a branching index of less than 2.1, preferably 1.8 or less, and more preferably 1.5 or less.

Unless otherwise specified, the term oligomer product encompasses oligomer product from a feedstock having not been exposed to the catalyst and oligomer product from a feedstock having been exposed to the catalyst (i.e., recycled oligomer product).

The properties described above for the oligomer product including the branching index and the dimer/trimer/tetramer+weight percentages apply to recycled oligomer product.

Applications

The oligomer product described herein can be used as a chemical intermediate in the production of high purity hydrocarbon fluids or solvents, alcohols, detergents/surfactants, esters such as plasticizer esters and synthetic lubricants, and the like. Common classes of surfactants include not limited to, for example, alkylbenzene sulfonate, alcohol sulfates, carboxylates, alcohol ethoxylates and alkylphenol ethoxylates, having low branching indexes of hydrophobe are particular useful as they have better hard water solubility and better biodegradability resulting from the lower levels of quaternary carbons.

For example, the oligomer product can be used as a feed for a hydroformylation reaction for the production of aldehydes and alcohols. The aldehydes may be oxidized to produce acids or hydrogenated to produce alcohols. The alcohols may then be used in the production of synthetic esters such as plasticizer esters or synthetic lubricants or in the production of surfactants, for example, alkylbenzene sulfonates, alcohol sulfates, carboxylates, alcohol ethoxylates and alkylphenol ethoxylates.

The oligomer product may be hydroformylated by, for example, the processes described in PCT Publication WO 2005/058787. It is preferred to use high pressure hydroformylation technology which is typically cobalt catalyzed, but rhodium may also be used as the catalyst. The olefin oligomers of the present invention are particularly useful as feedstocks that are hydroformylated in the manner described in PCT Publication WO 2005/058787 where the low level of antioxidant enables improved hydroformylation reactions. Where the aldehydes produced by this method are hydrogenated, this may readily be accomplished by the method described in PCT Publication WO 2005/058782.

An example alcohol composition using an oligomer composition derived from a $C_4$ feedstock may comprise 25 wt % to 75 wt % $C_8$ alcohol, 25 wt % to 50 wt % $C_{12}$ alcohol, and 0 wt % to 25 wt % $C_{16}$ alcohol, based on the weight of the feedstock. Another example alcohol composition using an oligomer composition derived from a $C_4$ feedstock may comprise 35 wt % to 75 wt % $C_8$ alcohol, 25 wt % to 45 wt % $C_{12}$ alcohol, and 5 wt % to 15 wt % $C_{16}$ alcohol. Yet another example alcohol composition using an oligomer composition derived from a $C_4$ feedstock may comprise 50 wt % to 75 wt % $C_8$ alcohol, 25 wt % to 35 wt % $C_{12}$ alcohol, and 0 wt % to 10 wt % $C_{16}$ alcohol. Any of the foregoing examples can have a branching index of less than 1.8, preferably 1.5 or less.

An example alcohol composition using an oligomer composition derived from a $C_4/C_8$ feedstock (e.g., Table 5 or a recycled oligomer product distilled or as is) may comprise 0 wt % to 30 wt % $C_8$ alcohol, 45 wt % to 85 wt % $C_{12}$ alcohol, 5 wt % to 55 wt % $C_{16}$ alcohol, and 0 wt % to 10 wt % $C_{20+}$ alcohol. Another example alcohol composition using an oligomer composition derived from a $C_4/C_8$ feedstock (e.g., Table 5 or a recycled oligomer product distilled or as is) may comprise 5 wt % to 25 wt % $C_8$ alcohol, 50 wt % to 85 wt % $C_{12}$ alcohol, 10 wt % to 30 wt % $C_{16}$ alcohol, and 0 wt % to 10 wt % $C_{20+}$ alcohol. Yet another example alcohol composition using an oligomer composition derived from a $C_4/C_8$ feedstock (e.g., Table 5 or a recycled oligomer product distilled or as is) may comprise 5 wt % to 25 wt % $C_8$ alcohol, 60 wt % to 85 wt % $C_{12}$ alcohol, 8 wt % to 20 wt % $C_{16}$ alcohol, and 0 wt % to 5 wt % $C_{20+}$ alcohol. Any of the foregoing examples can have a branching index of less than 2.1, preferably 1.8 or less, and more preferably 1.5 or less.

An example alcohol composition using an oligomer composition derived from a $C_3$ feedstock may comprise 25 wt % to 75 wt % $C_6$ alcohol, 25 wt % to 50 wt % $C_9$ alcohol, and 0 wt % to 25 wt % $C_{12}$ alcohol. Another example alcohol composition using an oligomer composition derived from a $C_3$ feedstock may comprise 35 wt % to 75 wt % $C_6$ alcohol, 25 wt % to 45 wt % $C_9$ alcohol, and 5 wt % to 15 wt % $C_{12}$ alcohol. Yet another example alcohol composition using an oligomer composition derived from a $C_3$ feedstock may comprise 50 wt % to 75 wt % $C_6$ alcohol, 25 wt % to 35 wt % $C_9$ alcohol, and 0 wt % to 10 wt % $C_{12}$ alcohol. Any of the foregoing examples can have a branching index of less than 2.1, preferably 1.8 or less, and more preferably 1.5 or less.

An example alcohol composition using an oligomer composition derived from a $C_5$ feedstock may comprise 25 wt % to 75 wt % $C_{10}$ alcohol, 25 wt % to 50 wt % $C_{15}$ alcohol, and 0 wt % to 25 wt % $C_{20}$ alcohol. Another example alcohol composition using an oligomer composition derived from a $C_5$ feedstock may comprise 35 wt % to 75 wt % $C_{10}$ alcohol, 25 wt % to 45 wt % $C_{15}$ alcohol, and 5 wt % to 15 wt % $C_{20}$ alcohol. Yet another example alcohol composition using an oligomer composition derived from a $C_5$ feedstock may comprise 50 wt % to 75 wt % $C_{10}$ alcohol, 25 wt % to 35 wt % $C_{15}$ alcohol, and 0 wt % to 10 wt % $C_{20}$ alcohol. Any of the foregoing examples can have a branching index of less than 2.1, preferably 1.8 or less, and more preferably 1.5 or less.

Further reactions to form surfactants can be performed on the oligomer products and alcohols produced from the oligomer product described herein. The surfactants would have a tail group mixture corresponding to the oligomer product and a head group that can be anionic, cationic, amphoteric, or nonionic. Example of anionic head groups include, but are not limited to, phosphates, sulfonates, benzyl sulfonates, sulfates, benzyl sulfates carboxylates, and the like. Examples of cationic head groups include, but are not limited to, quaternary ammonium salts and the like. Examples of amphoteric head groups include, but are not limited to, aminopropionic acid, iminodipropionate, betaine, and the like. Examples of nonionic head groups include, but are not limited to, polyethylene oxide, polyethylene glycol, polypropylene oxide, polypropylene glycol, and the like.

As mentioned above, detergent formulations can be made from surfactants derived from the oligomer products described herein. Detergent formulations comprise an aqueous fluid; and a reaction product of one or more oligomer product, the reaction product comprising a hydrophobic portion and a polar head group bonded to the hydrophobic portion; wherein an olefin moiety in the one or more oligomer product reacts to produce the hydrophobic portion; and wherein the one or more oligomer product have a Branch Index ranging from 0.5 and 2.1 and branching is retained in the hydrophobic portion of the reaction product; wherein the surfactant is present in the aqueous fluid at a concentration ranging from about 10 wt % to about 80 wt %.

As used herein, "Cx surfactant" refers to an oligomer having 'x' carbon number that is used to make the surfactant, thus, a C8 surfactant is a surfactant produced from a C8 oligomer through hydroformylation and/or some other means. Also, as used herein, when referring to a "Cx alcohol", the alcohol has a carbon number of x+1.

The surfactant used in a detergent formulation may comprise any number of surfactants having different chain lengths and thus form a surfactant composition. An example surfactant composition using an oligomer composition derived from a $C_4$ feedstock may comprise 0 wt % to 15 wt % $C_8$ surfactant, 10 wt % to 70 wt % $C_{12}$ surfactant, and 0 wt % to 15 wt % $C_{16+}$ surfactant, based on the weight of the surfactant composition. Another example surfactant composition using an oligomer composition derived from a $C_4$ feedstock may comprise 0 wt % to 30 wt % $C_8$ surfactant, 40 wt % to 85 wt % $C_{12}$ surfactant, and 0 wt % to 30 wt % $C_{16+}$ surfactant. Yet another example surfactant composition using an oligomer composition derived from a $C_4$ feedstock may comprise 0 wt % to 10 wt % $C_8$ surfactant, 80 wt % to 100 wt % $C_{12}$ surfactant, and 0 wt % to 10 wt % $C_{16+}$ surfactant. Any of the foregoing examples can have a branching index of less than 2.1, preferably 1.8 or less, and more preferably 1.5 or less.

An example surfactant composition using an oligomer composition derived from a $C_4/C_8$ feedstock (e.g., Table 5 or a recycled oligomer product distilled or as is) may comprise 0 wt % to 315 wt % $C_8$ surfactant, 10 wt % to 70 wt % $C_{12}$ surfactant, and 0 wt % to 15 wt % $C_{16+}$ surfactant. Another example surfactant composition using an oligomer composition derived from a $C_4/C_8$ feedstock (e.g., Table 5 or a recycled oligomer product distilled or as is) may comprise 0 wt % to 30 wt % $C_8$ surfactant, 40 wt % to 85 wt % $C_{12}$ surfactant, and 0 wt % to 30 wt % $C_{16+}$ surfactant. Yet another example surfactant composition using an oligomer composition derived from a $C_4/C_8$ feedstock (e.g., Table 5 or a recycled oligomer product distilled or as is) may comprise 0 wt % to 10 wt % $C_8$ surfactant, and 80 wt % to 100 wt % $C_{12+}$ surfactant. Any of the foregoing examples can have a branching index of less than 2.1, preferably 1.8 or less, and more preferably 1.5 or less.

An example surfactant composition using an oligomer composition derived from a $C_3$ feedstock may comprise 0 wt % to 15 wt % $C_6$ surfactant, 0 wt % to 15 wt % $C_9$ surfactant, and 10 wt % to 70 wt % $C_{12+}$ surfactant. Another example surfactant composition using an oligomer composition derived from a $C_3$ feedstock may comprise 0 wt % to 30 wt % $C_6$ surfactant, 0 wt % to 30 wt % $C_9$ surfactant, and 40 wt % to 85 wt % $C_{12+}$ surfactant. Yet another example surfactant composition using an oligomer composition derived from a $C_3$ feedstock may comprise 0 wt % to 10 wt % $C_6$ surfactant, 0 wt % to 10 wt % $C_9$ surfactant, and 80 wt % to 100 wt % $C_{12+}$ surfactant. Any of the foregoing examples can have a branching index of less than 2.1, preferably 1.8 or less, and more preferably 1.5 or less.

An example surfactant composition using an oligomer composition derived from a $C_5$ feedstock may comprise 0 wt % to 15 wt % $C_{10}$ surfactant, 10 wt % to 70 wt % $C_{15}$ surfactant, and 0 wt % to 15 wt % $C_{20+}$ surfactant. Another example surfactant composition using an oligomer composition derived from a $C_5$ feedstock may comprise 0 wt % to 30 wt % $C_{10}$ surfactant, 40 wt % to 85 wt % $C_{15}$ surfactant, and 0 wt % to 30 wt % $C_{20+}$ surfactant. Yet another example surfactant composition using an oligomer composition derived from a $C_5$ feedstock may comprise 80 wt % to 100 wt % $C_{10}$ surfactant, 0 wt % to 10 wt % $C_{15}$ surfactant, and 0 wt % to 10 wt % $C_{20+}$ surfactant. Any of the foregoing examples can have a branching index of less than 2.1, preferably 1.8 or less, and more preferably 1.5 or less.

Example Embodiments

A first example embodiment of the present invention is a process for olefin oligomerization, the process comprising: contacting a feedstock comprising at least one $C_3$ to $C_{20}$ olefin/paraffin under oligomerization conditions in the presence of a Si/Al ZSM-23 catalyst having no amine treatment and a $Si/Al_2$ molar ratio of 20 to 60 and/or a Si/Al/Ti ZSM-23 catalyst having no amine treatment, a $Si/Al_2$ molar ratio of 20 to 60, and a Ti/Al molar ratio of 0.1 to 3; and recovering an oligomeric product comprising dimers having a branching index of less than 2.1, trimers having a branching index of less than 2.1, and tetramers having a branching index of less than 2.1, or in any one or more of these, a branching index within a range from 0.5, or 1.0, or 1.1, or 1.2, or 1.3 to 1.6, or 1.8, or 2.0, or 2.1. Optionally, one or more of the following may be included: Element 1: wherein the at least one $C_3$ to $C_{20}$ olefin/paraffin comprises at least one $C_3$ to $C_5$ olefin/paraffin at a concentration of at least 40 wt % of the at least one $C_3$ to $C_{20}$ olefin/paraffin; Element 2: wherein the at least one $C_3$ to $C_{20}$ olefin/paraffin comprises $C_3$ olefins/paraffins at a concentration of at least 40 wt % of the at least one $C_3$ to $C_{20}$ olefin/paraffin; Element 3: wherein the oligomeric product comprises 25 wt % to 75 wt % $C_6$ oligomer, 25 wt % to 50 wt % $C_9$ oligomer, and 0 wt % to 25 wt % $C_{12}$ oligomer; Element 4: wherein the at least one $C_3$ to $C_{20}$ olefin/paraffin comprises $C_4$ olefins/paraffins at a concentration of at least 40 wt % of the at least one $C_3$ to $C_{20}$ olefin/paraffin; Element 5: wherein the oligomeric product comprises 25 wt % to 75 wt % $C_8$ oligomer, 25 wt % to 50 wt % $C_{12}$ oligomer, and 0 wt % to 25 wt % $C_{16}$ oligomer; Element 6: wherein the at least one $C_3$ to $C_{20}$ olefin/paraffin comprises $C_5$ olefins/paraffins at a concentration of at least 40 wt % of the at least one $C_3$ to $C_{20}$ olefin/paraffin; Element 7: wherein the oligomeric product comprises 25 wt % to 75 wt % $C_{10}$ oligomer, 25 wt % to 50 wt % $C_{15}$ oligomer, and 0 wt % to 25 wt % $C_{10}$ oligomer; Element 8: wherein the oligomeric product comprises dimers at 25 wt % to 75 wt %, trimers at 25 wt % to 50 wt %, and tetramers at 0 wt % to 25 wt %; Element 9: wherein the oligomeric product comprises dimers at 35 wt % to 75 wt %, trimers at 25 wt % to 45 wt %, and tetramers at 5 wt % to 15 wt %.; Element 10: wherein the oligomeric product comprises dimers at 50 wt % to 75 wt %, trimers at 25 wt % to 35 wt %, and tetramers at 0 wt % to 10 wt %; Element 11: wherein the oligomeric product comprises 0 wt % to 10 wt % of pentamers and higher oligomers; Element 12: wherein the oligomeric product comprises 0 wt % to 1 wt % of pentamers and higher oligomers; Element 13: wherein the at least one $C_3$ to $C_{20}$ olefin/paraffin comprises $C_3$ olefins/paraffins at a concentration of at least 40 wt % of the at least one $C_3$ to $C_{20}$ olefin/paraffin and $C_6$ olefins/paraffins at a concentration of at least 10 wt % of the at least one $C_3$ to $C_{20}$ olefin/paraffin; Element 14: wherein the oligomeric product comprises 0 wt % to 30 wt % $C_6$ oligomer, 45 wt % to 85 wt % $C_9$ oligomer, 5 wt % to 55 wt % $C_{12}$ oligomer, and 0 wt % to 10 wt % $C_{20+}$ oligomer; Element 15: wherein the at least one $C_3$ to $C_{20}$ olefin/paraffin comprises $C_4$ olefins/paraffins at a concentration of at least 40 wt % of the at least one $C_3$ to $C_{20}$ olefin/paraffin and $C_8$ olefins/paraffins at a concentration of at least 10 wt % of the at least one $C_3$ to $C_{20}$ olefin/paraffin; Element 16: wherein the oligomeric product comprises 0 wt % to 30 wt % $C_8$ oligomer, 45 wt % to 85 wt % $C_{12}$ oligomer, 5 wt % to 55 wt % $C_{16}$ oligomer, and 0 wt % to 10 wt % $C_{20+}$ oligomer; Element 17: wherein the at least one $C_3$ to $C_{20}$ olefin/paraffin comprises $C_5$ olefins/paraffins at a concentration of at least 40 wt % of the at least one $C_3$ to $C_{20}$ olefin/paraffin and $C_{10}$ olefins/paraffins at a concentration of at least 10 wt % of the at least one $C_3$ to $C_{20}$ olefin/paraffin; Element 18: wherein the oligomeric product comprises 0 wt % to 30 wt % $C_{10}$ oligomer, 45 wt % to 85 wt % $C_{15}$ oligomer, 5 wt % to 55 wt % $C_{20}$ oligomer, and 0 wt % to 10 wt % $C_{20+}$ oligomer; Element 19: wherein the Si/Al ZSM-23 catalyst has the Si/Al$_2$ molar ratio of 30 to 45; Element 20: wherein the Si/Al/Ti ZSM-23 catalyst has the Si/Al$_2$ molar ratio of 30 to 45; Element 21: wherein the Si/Al ZSM-23 catalyst and/or the Si/Al/Ti ZSM-23 catalyst has been treated before contacting with the feedstock, wherein the treatment is selected from the group consisting of steaming, acid washing, depositing coke, and any combination thereof; Element 22: wherein the process further comprises treating the Si/Al ZSM-23 catalyst and/or the Si/Al/Ti ZSM-23 catalyst before contacting with the feedstock, wherein the treatment is selected from the group consisting of steaming, acid washing, depositing coke, and any combination thereof; Element 23: wherein the Si/Al ZSM-23 catalyst and/or the Si/Al/Ti ZSM-23 catalyst is an extrudate comprising a binder at 1 wt % to 90 wt % and the catalyst at 10 wt % to 99 wt %; Element 24: wherein the Si/Al ZSM-23 catalyst and/or the Si/Al/Ti ZSM-23 catalyst is produced via crystal growth; Element 25: wherein the oligomerization conditions are a temperature of 170° C. to 270° C. and a weight hourly space velocity of 5 hr$^{-1}$ to 30 hr$^{-1}$; Element 26: wherein the oligomerization conditions are a temperature of 170° C. to 190° C. and a weight hourly space velocity of 5 hr$^{-1}$ to 10 hr$^{-1}$; Element 27: wherein the oligomerization conditions are a temperature of 190° C. to 210° C. and a weight hourly space velocity of 10 hr$^{-1}$ to 15 hr$^{-1}$; Element 28: wherein the oligomerization conditions are a temperature of 210° C. to 270° C. and a weight hourly space velocity of 15 hr$^{-1}$ to 30 hr$^{-1}$; Element 29: wherein the branching index is 1.0 to 1.8; Element 30: wherein the branching index is 1.0 to 1.5; Element 31: the process further comprising: converting the oligomer product to aldehydes and/or alcohols; Element 32: the process further comprising: converting the oligomer product to alcohols; and converting the oligomer products and alcohols to surfactants; Element 33: Element 32 and wherein a surfactant tail group is derived from the oligomeric product and a surfactant head group is selected from the group consisting of: phosphates, sulfonates, benzyl sulfonates, sulfates, and benzyl sulfates carboxylates; Element 34: Element 32 and wherein a surfactant tail group is derived from the oligomeric product and a surfactant head group is a quaternary ammonium salt; Element 35: Element 32 and wherein a surfactant tail group is derived from the oligomeric product and a surfactant head group is selected from the group consisting of: aminopropionic acid, iminodipropionate, and betaine; and Element 36: Element 32 and wherein a surfactant tail group is derived from the oligomeric product and a surfactant head group is selected from the group consisting of: polyethylene oxide, polyethylene glycol, polypropylene oxide, and polypropylene glycol. Examples of combinations include, but are not limited to, Elements 2 and 3 in combination optionally in further combination with Element 11 or 12; Elements 4 and 5 in combination optionally in further combination with Element 11 or 12; Elements 6 and 7 in combination optionally in further combination with Element 11 or 12; Elements 13 and 14 in combination optionally in further combination with Element 11 or 12; Elements 15 and 16 in combination optionally in further combination with Element 11 or 12; Elements 17 and 18 in combination optionally in further combination with Element 11 or 12; Element 1 and one or Elements 8-10 in combination optionally in further combination with Element 11 or 12; any of the foregoing combinations in combination with one or more of Elements 19-36; and two or more of Elements 33-36 in combination.

Another embodiment is a detergent formulation comprising the surfactants produced by the first embodiment with Element 32 and optionally one or more of Elements 1-30 and 33-36.

Yet another embodiment is a detergent formulation comprising: 0 wt % to 15 wt % $C_8$ surfactant, 10 wt % to 70 wt % $C_{12}$ surfactant, and 0 wt % to 15 wt % $C_{16}$ surfactant, based on the weight of the detergent composition, wherein each surfactant has a branching index of less than 1.8, preferably 1.5 or less.

Another embodiment is a detergent formulation comprising: 0 wt % to 30 wt % $C_8$ surfactant, 40 wt % to 85 wt % $C_{12}$ surfactant, 0 wt % to 30 wt % $C_{16+}$ surfactant, wherein each surfactant has a branching index of less than 1.8, preferably 1.5 or less.

Yet another embodiment is a detergent formulation comprising: 0 wt % to 15 wt % $C_6$ surfactant, 0 wt % to 15 wt % $C_9$ surfactant, and 10 wt % to 70 wt % $C_{12}$ surfactant, wherein each surfactant has a branching index of less than 1.8, preferably 1.5 or less.

Another embodiment is a detergent formulation comprising: 0 wt % to 30 wt % $C_6$ surfactant, 0 wt % to 30 wt % $C_9$ surfactant, 40 wt % to 85 wt % $C_{12+}$ surfactant, wherein each surfactant has a branching index of less than 1.8, preferably 1.5 or less.

Yet another embodiment is a detergent formulation comprising: 40 wt % to 85 wt % $C_{10}$ surfactant, 0 wt % to 30 wt % $C_{15}$ surfactant, and 0 wt % to 30 wt % $C_{20}$ surfactant, wherein each surfactant has a branching index of less than 1.8, preferably 1.5 or less.

Another embodiment is a detergent formulation comprising: 10 wt % to 70 wt % $C_{10}$ surfactant, 0 wt % to 15 wt % $C_{15}$ surfactant, 0 wt % to 15 wt % $C_{20+}$ surfactant, wherein each surfactant has a branching index of less than 1.8, preferably 1.5 or less.

Each of the foregoing detergent embodiments and each surfactant independently may have one of the following head groups: phosphates, sulfonates, benzyl sulfonates, sulfates, benzyl sulfates carboxylates, quaternary ammonium salt, aminopropionic acid, iminodipropionate, betaine, polyethylene oxide, polyethylene glycol, polypropylene oxide, and polypropylene glycol. Further, each of the foregoing detergent embodiments may include two or more surfactants having different head groups.

Unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a to developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

ZSM-23 catalyst were prepared using the recipe described in U.S. Pat. Nos. 4,076,842, 5,332,566, and 8,500,991 to have a $Si/Al_2$ molar ratio of either 120 or 40. The catalysts were not impregnated with a metal. The catalysts were not treated with an amine The oligomerization reaction was carried out in fixed bed reactor with internal diameter 7 mm 2-3 grams of catalyst particles with size 0.3-0.6 mm diluted with SiC was loaded into reactor. Prior to the reaction, the catalyst was dried at 150° C. under $N_2$ for 5 hours. The reaction was operated in down flow mode. Mass flow controllers delivered the hydrocarbon feed to the catalyst, Product carbon number distribution and branching was detected by HP-5890 GC equipped by a 30 meter DB-1 column (0.1 mm id) and 0.2 μm film thickness with an $H_2$-GC. The reaction conditions were at a temperature 150° C. to 250° C., a WHSV of 2 $hr^{-1}$ to 20 $hr^{-1}$, and a pressure of 70 bar. The exact temperature and WHSV for each reaction is provided in the details below.

The feedstock was 1-butene:butane:isobutane at relative wt % of 50:40:10. The isobutane was used as an internal standard.

Example 1. Each of the ZSM-23 catalysts with $Si/Al_2$ molar ratio of either 120 or 40 were separately reacted with feedstock at 170° C. and a WHSV of 4 $hr^{-1}$. Table 7 provides the reaction product details.

TABLE 7

| $Si/Al_2$ Molar Ratio | % Conversion | % $C_{10}$-$C_{16}$ Yield | $C_{12}$ BI |
|---|---|---|---|
| 120 | 36 | 6 | 1.8 |
| 40 | 49 | 14 | 1.8 |

The ZSM-23 catalysts with $Si/Al_2$ molar ratio of 40 had a higher butene conversation and a higher $C_{10}$-$C_{16}$ yield.

Example 2. The ZSM-23 catalysts with $Si/Al_2$ molar ratio of 40 was reacted with the feedstock under several temperature and WHSV oligomerization conditions. Table 8 to provides the reaction product details. At relatively high reaction temperature, $C_{12}$ selectivity is higher with lower branching. Improved yield of low branched $C_{12}$ can be obtained over steamed ZSM-23.

TABLE 8

| | Catalyst | | | |
|---|---|---|---|---|
| | ZSM-23 | ZSM-23 | ZSM-23 | Steamed ZSM-23 |
| Temperature (° C.) | 150 | 170 | 190 | 190 |
| WHSV ($hr^{-1}$) | 8 | 10 | 10 | 10 |
| Days on stream | 3 | 4 | 7 | 5 |
| Conversion (%) | 60 | 61 | 64 | 65 |
| Selectivity | | | | |
| $C_{4-7}$ (%) | 0.9 | 0.7 | 0.5 | 0.6 |
| $C_8$ (%) | 76.0 | 60.5 | 54.3 | 45.0 |
| $C_{9-11}$ (%) | 0.7 | 0.5 | 0.4 | 0.7 |
| $C_{12}$ (%) | 21.6 | 31.4 | 39.1 | 43.1 |
| $C_{13-15}$ (%) | 0 | 0.4 | 0 | 0.1 |
| $C_{16}$ (%) | 0.8 | 6.5 | 5.7 | 10.5 |
| $C_{17+}$ (%) | 0 | 0 | 0 | 0 |
| Product branching | | | | |
| BI $C_8$ | 1.8 | 1.8 | 1.6 | 1.6 |
| BI $C_{12}$ | 1.9 | 1.7 | 1.5 | 1.4 |
| BI $C_{16}$ | — | — | — | 1.8 |

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention.

All numbers and ranges disclosed above may vary by some amount. Whenever a numerical range with a lower limit and an upper limit is disclosed, any number and any included range falling within the range is specifically disclosed.

The invention claimed is:

1. A process for olefin oligomerization, the process comprising:
    contacting a feedstock comprising at least one $C_3$ to $C_{20}$ olefin/paraffin under oligomerization conditions in the presence of a Si/Al ZSM-23 catalyst having no amine treatment and a $Si/Al_2$ molar ratio of 20 to 60 and/or a Si/Al/Ti ZSM-23 catalyst having no amine treatment, a $Si/Al_2$ molar ratio of 20 to 60, and a Ti/Al molar ratio of 0.1 to 3; and
    recovering an oligomeric product comprising dimers having a branching index of less than 2.1, trimers having a branching index of less than 2.1, and tetramers having a branching index of less than 2.1.

2. The process of claim 1, wherein the at least one $C_3$ to $C_{20}$ olefin/paraffin comprises at least one $C_3$ to $C_5$ olefin/paraffin at a concentration of at least 40 wt % of the at least one $C_3$ to $C_{20}$ olefin/paraffin.

3. The process of claim 1, wherein the oligomeric product comprises dimers at 25 wt % to 75 wt %, trimers at 25 wt % to 50 wt %, and tetramers at 0 wt % to 25 wt %.

4. The process of claim 1, wherein the oligomeric product comprises dimers at 35 wt % to 75 wt %, trimers at 25 wt % to 45 wt %, and tetramers at 5 wt % to 15 wt %.

5. The process of claim 1, wherein the oligomeric product comprises dimers at 50 wt % to 75 wt %, trimers at 25 wt % to 35 wt %, and tetramers at 0 wt % to 10 wt %.

6. The process of claim 1, wherein the at least one $C_3$ to $C_{20}$ olefin/paraffin comprises $C_3$ olefins/paraffins at a concentration of at least 40 wt % of the at least one $C_3$ to $C_{20}$ olefin/paraffin.

7. The process of claim 6, wherein the oligomeric product comprises 25 wt % to 75 wt % $C_6$ oligomer, 25 wt % to 50 wt % $C_9$ oligomer, and 0 wt % to 25 wt % $C_{12}$ oligomer.

8. The process of claim 1, wherein the at least one $C_3$ to $C_{20}$ olefin/paraffin comprises $C_4$ olefins/paraffins at a concentration of at least 40 wt % of the at least one $C_3$ to $C_{20}$ olefin/paraffin.

9. The process of claim 8, wherein the oligomeric product comprises 25 wt % to 75 wt % $C_8$ oligomer, 25 wt % to 50 wt % $C_{12}$ oligomer, and 0 wt % to 25 wt % $C_{16}$ oligomer.

10. The process of claim 1, wherein the at least one $C_3$ to $C_{20}$ olefin/paraffin comprises $C_5$ olefins/paraffins at a concentration of at least 40 wt % of the at least one $C_3$ to $C_{20}$ olefin/paraffin.

11. The process of claim 10, wherein the oligomeric product comprises 25 wt % to 75 wt % $C_{10}$ oligomer, 25 wt % to 50 wt % $C_{15}$ oligomer, and 0 wt % to 25 wt % $C_{10}$ oligomer.

12. The process of claim 1, wherein the oligomeric product comprises 0 wt % to 1 wt % of pentamers and higher oligomers.

13. The process of claim 1, wherein the process further comprises treating the Si/Al ZSM-23 catalyst and/or the Si/Al/Ti ZSM-23 catalyst before contacting with the feedstock, wherein the treatment is selected from the group consisting of steaming, acid washing, depositing coke, and any combination thereof.

14. The process of claim 1, wherein the Si/Al ZSM-23 catalyst and/or the Si/Al/Ti ZSM-23 catalyst is an extrudate comprising a binder at 1 wt % to 90 wt % and the catalyst at 10 wt % to 99 wt %.

15. The process of claim 1, wherein the oligomerization conditions are a temperature of 170° C. to 270° C. and a weight hourly space velocity of 5 $hr^{-1}$ to 30 $hr^{-1}$.

16. The process of claim 1, wherein the oligomerization conditions are a temperature of 170° C. to 190° C. and a weight hourly space velocity of 5 $hr^{-1}$ to 10 $hr^{-1}$.

17. The process of claim 1, wherein the oligomerization conditions are a temperature of 190° C. to 210° C. and a weight hourly space velocity of 10 $hr^{-1}$ to 15 $hr^{-1}$.

18. The process of claim 1, wherein the oligomerization conditions are a temperature of 210° C. to 270° C. and a weight hourly space velocity of 15 $hr^{-1}$ to 30 $hr^{-1}$.

19. The process of claim 1, wherein the branching index is 1.0 to 1.5.

20. The process of claim 1 further comprising:
converting the oligomer product to aldehydes and/or alcohols.

21. The process of claim 1 further comprising:
converting the oligomer product to alcohols;
converting the oligomer product and alcohols to surfactants; and
converting the alcohols to surfactants.

* * * * *